(12) United States Patent
Stährfeldt et al.

(10) Patent No.: US 6,225,385 B1
(45) Date of Patent: May 1, 2001

(54) OLIGOMERIC STABILIZER MIXTURE

(75) Inventors: Thomas Stährfeldt, Neusäss; Alexander Lichtblau, Augsburg; Gerhard Pfahler, Eichenau; Karl Gaa, Burtenbach, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/272,837

(22) Filed: Mar. 19, 1999

(30) Foreign Application Priority Data

Mar. 20, 1998  (DE) .............................. 198 12 224

(51) Int. Cl.$^7$ .............................. C08K 5/49; C08K 5/51; C08K 5/53; C08K 5/52
(52) U.S. Cl. .......................... 524/119; 524/128; 524/134; 524/150; 524/151; 524/152; 524/153; 252/400.21
(58) Field of Search ...................... 252/400.21; 524/119, 524/128, 134, 150, 151, 152

(56) References Cited

U.S. PATENT DOCUMENTS 3,354,117  11/1967  Schmidt et al. ................... 260/45.85

FOREIGN PATENT DOCUMENTS

| 1153894 | 3/1964 | (DE) . |
| 3029176 | 3/1982 | (DE) . |
| 1595889 | 6/1970 | (FR) . |
| 1242124 | 8/1971 | (GB) . |

OTHER PUBLICATIONS

R. Gächter, H. Müller, Plastic Additives Handbook, 3$^{rd}$ Edition 1989, Chapter 2, p. 109 ff.
Derwent Patent Family Report and/or Abstract.
Chemical Abstract 59:14170a.

*Primary Examiner*—Kriellion A Sanders
(74) *Attorney, Agent, or Firm*—Susan S. Jackson; Scott E. Hanf

(57) ABSTRACT

The present invention relates to a stabilizer mixture prepared by partially condensing $PCl_3$ with 2,2'-dimethyl-4,4'-dihydroxy-5,5'-di-tert-butyldiphenyl sulfide, where the phosphorus content is from 2 to 4% by weight and the content of 2,2'-dimethyl-4,4'-dihydroxy-5,5'-di-tert-butyldiphenyl sulfide is from 0.5 to 50% by weight.

The stabilizer mixture has very good solubility in organic solvents and in the polymer and has very good stabilizing action.

22 Claims, No Drawings

OLIGOMERIC STABILIZER MIXTURE

BACKGROUND OF THE INVENTION

The present invention relates to a novel stabilizer mixture which markedly slows the metal-compound-accelerated degradation and aging of organic materials, in particular of organic polymers.

There is a wide variety of ways by which organic materials, in particular plastics, can come into contact with metals, metal ions and metal-containing compounds. Contact of this type is impossible to avoid particularly in cases of residues of metallic catalysts used to prepare the plastic. There are also many ways in which organic polymers during their processing come into contact with metallic surfaces. In addition, various metal-containing compounds are intentionally admixed with the plastic to achieve specific effects: examples of these are metal-containing stabilizers, pigments and fillers. In addition, organic polymers are very frequently in direct contact with metals in end applications, as is often the case with cable sheathings, pipes and electronic components.

Like all organic compounds, plastics too are subject to natural aging. This process, which is associated with impairment of functional properties and always ends with the decomposition of the organic material, can be accelerated by accelerators and slowed by stabilizers. Metals and metal-containing compounds are generally known to be accelerators for degradation and ageing processes of this type (cf. R. Gächter, H. Müller, Taschenbuch der Kunststoff-Additive [Plastics Additives Handbook], Carl Hanser Verlag Munich, Vienna; 3rd edn. 1989; Chapter 2, pp. 109 ff).

The use of a condensation product made from phosphorus trichloride (1) and 2,2'-dimethyl-4,4'-dihydroxy-5,5'-di-tert-butyidiphenyl sulfide (2) in a mixture with other chemicals is described in DE-A-1 153 894. However, there is no indication of a stabilizing action of the product on its own. This condensation product is used in this document only in combination with the condensation product made from nonylphenol and acetone and with dilauryl thiodipropionate (Comparative Experiment No. 5). DE-A-1 153 894 describes the stabilizing action of the mixture described against the damaging action of heat and oxygen on copper-contaminated polypropylene.

The effectiveness of a condensation product made from (1) and (2) alone and its use as a stabilizer for organic material had not been described until the publication of DE-A-3 029 176. The compound described there is a three-dimensionally crosslinked polymer insoluble in all organic solvents and having a phosphorus content of 4.9% (DE-A-3 029 176, p. 2, line 17; p. 5, Example 3). This document describes the stabilizing action of the high-molecular-weight, insoluble condensation product, with a degree of polymerization of from 50 to 500, on a polymer (p. 3, line 45). Stabilization against the damaging actions of oxygen and heat is described. The starting materials (1) and (2) used there are brought together to prepare the condensation product within a period of 15 min at only 50° C. in xylene in the presence of a small amount of dimethylformamide, after stirring (50° C.) for 1 hour are heated to 135° C. and condensed at this temperature for 1 hour with elimination of hydrogen chloride.

The condensation product known from the prior art is insoluble in organic solvents and has unsatisfactory stabilizing action. The object was therefore to provide a product which has better solubility and is more effective.

SUMMARY OF THE INVENTION

Surprisingly, it has been found that suitable conduct of the reaction can prepare from the compounds (1) and (2) a stabilizer mixture which has excellent solubility in organic solvents and is soluble in the polymer and has excellent stabilizing action. The present invention relates to a novel stabilizer mixture which markedly slows the metal-compound-accelerated degradation and aging of organic materials, in particular of organic polymers.

The invention therefore relates to a stabilizer mixture obtainable by partial condensation of $PCl_3$ with 2,2'-dimethyl-4,4'-dihydroxy-5,5'-di-tert-butyldiphenyl sulfide, where the phosphorus content is from 2 to 4% by weight and the content of unreacted 2,2'-dimethyl-4,4'-dihydroxy-5,5'-di-tert-butyldiphenyl sulfide is from 0.5 to 50% by weight. During this, hydrogen chloride is eliminated and phosphorus-oxygen bonds are produced from some of the phenolic hydroxyl groups. Unreacted 2,2'-dimethyl-4,4'-dihydroxy-5,5'-di-tert-butyldiphenyl sulfide (2), cf. diagram 1, also remains as one of the constituents of the novel stabilizer mixture.

DESCRIPTION OF THE PREFERRED EMBODIMENTS

Phosphorus trichloride (1) is trifunctional and 2,2'-dimethyl-4,4'-dihydroxy-5,5'-di-tert-butyidiphenyl sulfide (2) is bifunctional. There is therefore a wide variety of ways in which linkage can take place to form phosphorus-oxygen bonds.

Diagram 1: Formation of the stabilizer mixture from compounds (1) and (2)

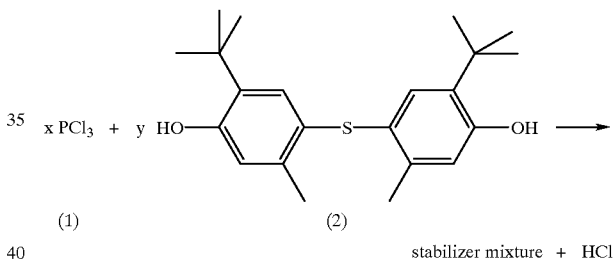

stabilizer mixture + HCl

The novel stabilizer mixture is formed with an x/y ratio of from 1:2.1 to 1:4.3.

At a molar ratio (1):(2) of 1:3 a discrete monomeric compound can be formed, containing a saturated phosphorus atom as its central constituent (diagram 2). At a molar ratio (1): (2) of 1:2.5 and 1:2.3, respectively, discrete monomeric compounds can be formed which have, respectively, two and three phosphorus atoms as a discrete constituent (diagram 2). At a molar ratio of 1:2 a polymeric chain can be formed in which a saturated phosphorus atom alternates with a 2,2'-dimethyl-4,4'-oxy-5,5'-di-tert-butyldiphenyl sulfide fragment. At a molar ratio of 1:1, a highly polymeric two-dimensional sheetlike network can be formed (diagram 2).

Diagram 2: Possible types of linkage from compounds (1) and (2) as starting materials

| Ratio of comp. (1):(2) | Possible linkage |
|---|---|
| 1:3 | \>P— |

-continued

| Ratio of comp. (1):(2) | Possible linkage |
|---|---|
| 1:(2.5) |  |
| 1:(2.33) | 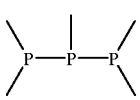 |
| 1:2 | 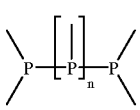 |
| 1:1 | 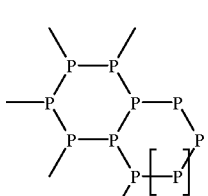 |

In addition, disproportionation or partial oxidation can also lead to the formation of $P^{IV}$ and $P^V$ compounds. Cleavage of the relatively labile phenyl-S-phenyl bonds can produce fragments of compound (2) which themselves can become reincorporated via a partial condensation into the novel stabilizer mixture.

The novel stabilizer mixture is prepared by partial condensation of phosphorus trichloride (1) and 2,2'-dimethyl-4,4'-dihydroxy-5,5'-di-tert-butyldiphenyl sulfide (2) forming phosphorus oxygen bonds and at the same time eliminating hydrogen chloride. The novel stabilizer mixture also comprises, contrasting with the compound described in DE-A-3 029 176, a proportion of 2,2'-dimethyl-4,4'-dihydroxy-5,5'-di-tert-butyldiphenyl sulfide in addition to the pure condensation product and has very good solubility in organic solvents and a P content of from 2.0 to 4.0% by weight.

The invention also relates to a process for preparing the novel stabilizer mixture.

Surprisingly, a stabilizer mixture with excellent suitability for stabilizing polymeric organic material is formed if an initial charge of 2,2'-dimethyl-4,4'-dihydroxy-5,5'-di-tert-butyldiphenyl sulfide (2) in a suitable atmosphere, preferably in an inert gas, and in an organic solvent, preferably in an aromatic solvent, in particular in toluene or o-xylene, is reacted at a temperature of from 20° C. to 1 50° C., preferably from 100° C. to 140° C., in particular from 115° C. to 130° C., with phosphorus trichloride (1), where the molar ratio (1):(2) is from 1:2.1 to 1:4.3 and the phosphorus trichloride (1) is added slowly and uniformly within from 0.5 to 8 hours, preferably within from 3 to 5 hours, and the reaction mixture is stirred at the same temperature for from 3 to 20 hours, preferably from 8 to 14 hours, and the product is freed from volatile constituents over a period of from 2 to 10 hours, preferably from 4 to 8 hours, at temperatures of up to 190° C. and at a pressure which may be reduced as far as 30 mbar.

The procedure described gives a stabilizer mixture which has a content of from 0.5 to 50% by weight, preferably from 5 to 30% by weight, in particular from 8 to 35% by weight, of 2,2'-dimethyl-4,4'-dihydroxy-5,5'-di-tert-butyldiphenyl sulfide, and which, in contrast to the highly polymeric, crosslinked and insoluble compound described in DE-A-3 029 176, has excellent solubility in organic solvents, such as o-xylene, and has a phosphorus content of from 2.0 to 4.0% by weight, preferably from 2.3 to 3.5% by weight, and has excellent suitability as a stabilizer for polymeric organic material.

It is also surprising (cf. Examples 1 and 2, experimental section) that, even at a molar ratio of 1:3 ($PCl_3$ to 2,2'-dimethyl-4,4'-dihydroxy-5,5'-di-tert-butyidiphenyl sulfide), the discrete molecule shown in diagram 2 is not formed. Rather, a molar ratio of, for example, 1:3 gives the novel mixture directly, cost-effectively and without the expense of a subsequent operation. Depending on the conduct of the reaction, the content of 2,2'-dimethyl-4,4'-dihydroxy-5,5'-di-tert-butyldiphenyl sulfide in the novel mixture can be, for example, from 0.5 to 50% by weight (cf. Examples 1 and 2, experimental section). No conclusions concerning the residual content of 2,2'-dimethyl4,4'-dihydroxy-5,5'-di-tert-butyldiphenyl sulfide remaining in the product mixture can be drawn from the molar ratio of the two starting materials to one another (1):(2). This residual content can be adjusted as desired over a wide range via the conduct of the reaction. In all cases this gives a product mixture which has good solubility in organic solvents and a P content of from 2.0 to 4.0% by weight.

The new stabilizer mixture is a brittle resin whose softening range is from 70 to 140° C., characteristically from 105 to 135° C. It can be added to the organic material to be stabilized prior to, during or after the polymerization and in solid or molten form, or dissolved in solvents or else as a masterbatch. When used as a solid the novel stabilizer mixture is particularly suitable in finely divided form. A particularly suitable masterbatch comprises the novel stabilizer mixture at a concentration of from 1 to 80% by weight, but preferably from 5 to 30% by weight, the remainder of the masterbatch being a polymer compatible with the polymer to be stabilized.

Incorporation in dissolved form is particularly suitable, where the solutions may comprise a concentration of, for example, from 5 to 80% by weight of the novel stabilizer mixture. Either the solution or the masterbatch may additionally comprise other stabilizers or active substances, such as UV absorbers, light stabilizers based on sterically hindered amines, quenchers, antioxidants, pigments, acid scavengers or fillers. The novel stabilizer mixture is preferably used in such a way that it is present in the polymer to be stabilized at a concentration of from 0.001 to 5% by weight, preferably from 0.02 to 2% by weight, based on the organic material, either alone or in combination with other additives. Examples of organic material are precursors for plastics, paints, coatings and oils, but in particular plastics, paints, coatings and oils themselves.

The novel stabilizer mixture is particularly suitable for stabilizing films, fibers, tapes, multifilaments, fabrics, extrusions, blowmoldings, injection moldings, thermoformings, powder coatings, printing inks, toner inks, photographic material, pigments, wood stains, leather, paints for buildings, protective paints for steelwork, lubricating oils, machine oils, bitumen or asphalt, in particular in applications in which the stabilized organic material is in contact with metals or with metallic compounds or comprises metallic compounds, for example in the form of catalyst residues.

The novel stabilizer mixture may also be used advantageously in combinations with other stabilizers. Examples of these are combinations with UV absorbers, with light stabilizers based on sterically hindered amines, with quenchers, with antioxidants, with pigments, with acid scavengers or with fillers. The mixtures resulting from these novel combinations have property profiles which are better than those of the individual components, for example synergistic effects in the inhibitory action on aging processes of the novel stabilized organic materials.

The present invention also relates to an organic material stabilized against the action of light, oxygen and heat, in particular a plastic, paint, coating or oil, which comprises the abovementioned concentrations of the novel stabilizer mixture.

Examples of materials of this type are described in German Patent Application 19 719 944.5 on pages 44 to 50, expressly incorporated herein by way of reference.

The novel stabilizer mixture or the organic material stabilized by a suitable combination with this stabilizer mixture may, if desired, also comprise other additives, for example antioxidants, light stabilizers, other metal deactivators, antistats, flame retardants, lubricants, nucleating agents, acid scavengers (basic costabilizers), pigments or fillers. Examples of antioxidants and light stabilizers which may be added, besides the novel compounds or combinations, are compounds based on sterically hindered amines or on sterically hindered phenols or costabilizers containing sulfur or phosphorus. Examples of compounds of this type are described in German Patent Application 19 719 944.5 on pages 51–65 under points 1–15, expressly incorporated herein by way of reference.

EXPERIMENTAL SECTION

Example 1

Preparation A of the novel stabilizer mixture by partial condensation of phosphorus trichloride (1) with 2,2'-dimethyl-4,4'-dihydroxy-5,5'-di-tert-butyidiphenyl sulfide (2)

64.4 g (180 mmol) of compound (2) are the initial charge at 20° C. in 45 ml of o-xylene. Under a gas blanket (nitrogen), 8.7 g (63 mmol) of compound (1) are added within a period of 0.5 h, whereupon the temperature of the reaction mixture increases to 60° C. The mixture is stirred for 6 hours at 120° C., heated to 160° C. and freed from volatile constituents for a further 6 h at a pressure reduced to 150 mbar, with stirring. The melt, cooled to about 20° C., is broken up into small pieces using liquid nitrogen. The product has a softening range of from 107 to 109° C., a phosphorus content of 2.6% by weight, a content of 50% by weight of 2,2'-dimethyl-4,4'-dihydroxy-5,5'-di-tert-butyldiphenyl sulfide (2) and a volatiles proportion of 23.5% (volatiles determined as follows: initial weight 500 mg; heating at 120 K/h; atmosphere: 1 l of nitrogen per minute; pan: Pt; surface: 3 cm$^2$; heating to 300° C. and holding at this temperature for 30 min; volatiles are the weight loss after 30 min/300° C.).

Example 2

Preparation B of the novel stabilizer mixture by partial condensation of phosphorus trichloride (1) with 2,2'-dimethyl-4,4'-dihydroxy-5,5'-di-tert-butyldiphenyl sulfide (2)

64.4 g (180 mmol) of compound (2) are heated to 120° C. in 45 ml of o-xylene under a gas blanket (nitrogen). 8.7 g (63 mmol) of compound (1) are added slowly and uniformly, with intensive stirring, over the course of 3 hours. The mixture is stirred for 6 hours at 120° C. and freed from volatile constituents for a further 6 h at 185° C. and at a pressure reduced to 150 mbar, with stirring. After 6 h the melt is cooled to about 20° C. and broken up into small pieces using liquid nitrogen. The product has a softening range of from 118–120° C., a phosphorus content of 3.0% by weight, a content of 25% by weight of 2,2'-dimethyl-4,4'-dihydroxy-5,5'-di-tert-butyldiphenyl sulfide (2) and a volatiles proportion of 16.9% (volatiles determined as follows: initial weight 500 mg; heating at 120 K/h; atmosphere: 1 l of nitrogen per minute; pan: Pt; surface: 3 cm$^2$; heating to 300° C. and holding at this temperature for 30 min; volatiles are the weight loss after 30 min/300° C.).

Examples 3 to 12

Stabilizing action of the novel partially condensed stabilizer mixture in polypropylene in contact with copper.

100 parts of polypropylene powder are pelletized with 0.2 part of calcium stearate and with the amounts of stabilizers given in Table 1 in an extruder, with a short-compression-zone screw of length 450 mm and L/D ratio of 20, through 3 heating zones at 200° C., 230° C. and 230° C., and then sheets of 1 mm thickness were injection molded from the pellets through 4 heating zones at 210° C., 220° C., 230° C. and 240° C., with a screw diameter of 36 mm and L/D ratio of 25. A copper foil with a freshly reduced surface is placed between these two sheets and pressed in a laboratory press between two polyester films to an overall thickness of 1 mm at 190° C. with 2 min of heating, 2 min of contact time and 2 min of pressure at 10 MN/m$^2$. A freshly reduced copper surface can be obtained by heating the copper sheet to red heat and quenching in methanol. The resultant test specimens are stored in a temperature-controlled circulating air oven at the stated temperature until degradation becomes visible via discoloration or cracking, or the specimens break when subjected to 1800 bending. High values to embrittlement in the accelerated aging in the circulating air oven demonstrate good stabilization.

TABLE 1

| Ex. No. | Stabilizer | Concentration [phr] | Embrittlement time at 140° C. [d] |
|---|---|---|---|
| 3 | Condensation product made from nonylphenol and acetone + reaction product of 2,2'-dimethyl-4,4'-dihydroxy-5,5'-di-tert-butyldiphenyl sulfide with PCl$_3$[1] | 0.5 + 0.5 | 2[1] |
| 4 | Partial condensation product made from 2,2'-dimethyl-4,4'-dihydroxy-5,5'-di-tert-butyldiphenyl sulfide with PCl$_3$ (in accordance with Example 2) | 0.5 | 8 |
| 5 | Condensation product made from nonylphenol and acetone + lauryl thiodipropionate/reaction product made from 2,2'-dimethyl-4,4'-dihydroxy-5,5'-di-tert-butyldiphenyl sulfide with PCl$_3$[1] | 0.5 + 0.5 + 0.5 | 7[1] |
| 6 | Glycol bis[3,3-bis(4'-hydroxy-3'-tert-butyl phenyl)butanoate] | 0.2 | 5 |
| 7 | Glycol bis[3,3-bis(4'-hydroxy-3'-tert-butylphenyl)butanoate] + partial condensation product made from 2,2'-dimethyl-4,4'-dihydroxy-5,5'-di-tert-butyldiphenyl sulfide with PCl$_3$ (in accordance with Example 2) | 0.2 + 0.5 | 31 |
| 8 | Distearyl thiodipropionate | 0.6 | 5 |
| 9 | Partial condensation product made from 2,2'-dimethyl-4,4'-dihydroxy-5,5'-di-tert-butyldiphenyl sulfide with PCl$_3$ (in accordance with Example 2) + distearyl thiodipropionate | 0.5 + 0.6 | 43 |

TABLE 1-continued

Long-term heat resistance of polypropylene in days in contact with coppersheet:

| Ex. No. | Stabilizer | Concentration [phr] | Embrittlement time at 140° C. [d] |
|---|---|---|---|
| 10 | Glycol bis[3,3-bis(4'-hydroxy-3'-tert-butylphenyl)butanoate) + distearyl thiodipropionate | 0.2 + 0.6 | 31 |
| 11 | Bisglycol ester of 3,3-bis(4'-hydroxy-3'-tert-butylphenyl)butanoic acid + distearyl thiodipropionate + partial condensation product made from 2,2'-dimethyl-4,4'-dihydroxy-5,5'-di-tert-butyldiphenyl sulfide with PCl₃ (as in Example 2) | 0.2 + 0.6 + 0.5 | 87 |
| 12 | none | — | 1 |

[1] DE-A-1153894, embrittlement time in contact with copper powder.

It is known that particular metal ions which can alter their oxidation state by one unit, generally metals with partially filled d-orbitals, can act as degradation catalysts in polymers, in particular in polyolefins. The embedding of a copper foil simulates this effect. As comparison of the results in Table 1 shows, the novel partially condensed stabilizer mixture develops excellent protective action against the damaging effect of metal ions.

The excellent stabilizing properties of the novel partially condensed stabilizer mixture as in Example 4 are found to be superior to the crosslinked reaction product from DE-A-1 153 894 as in Example 3 or Example 5, which moreover also comprises phenols with an antioxidant stabilizing effect. The polymer stabilized with the novel partially condensed stabilizer mixture thus gives a longer working life without further additives.

In addition, synergistic stabilizer mixtures made from the novel partially condensed stabilizer mixture and phenolic antioxidants and, if desired, sulfur costabilizers, show considerably better action than the individual products themselves. For example, when conventional thio-costabilizers or phenolic antioxidants are used the time to embrittlement is shorter than when using the partial condensation product of 2,2'-dimethyl-4,4'-dihydroxy-5,5'-di-tert-butyldiphenyl sulfide with PCl₃ and is merely in the region of a few days. In contrast, if mixtures of these components are used the increase in working life is far greater than the additive amount to be expected. The pairs of Examples 6/7, 8/9 and 10/11 illustrate this synergistic effect. For an additive effect the expected time to embrittlement should be 13 days (8+5), but in fact 31 days are achieved.

Examples 13 to 15

Stabilization of polyolefins under processing conditions.

100 parts of polypropylene powder are pelletized with 0.1 part of calcium stearate and with the amounts of stabilizers given in Table 2, in an extruder with a short-compression-zone screw of length 450 mm and L/D ratio of 20, through 3 heating zones at 200° C., 230° C. and 230° C. The melt index of the formulation is then measured. To test stability to degradation under processing conditions, the pelletization process is repeated 5 times and the melt index measured after the third and fifth pelletization steps. An increase in the melt index reveals degradation of the polymer through processing. Consistently low values are desirable. The results are given in Table 2.

TABLE 2

Melt index after repeated pelletization of polypropylene

| Ex. No. | Stabilizer | Concentration [phr] | Pelletization step 1st | 3rd | 5th |
|---|---|---|---|---|---|
| 13 | none | | 10.6 | 13.4 | 16.4 |
| 14 | Glycol bis[3,3-bis(4'-hydroxy-3'-tert-butylphenyl)butanoate] + distearyl disulfide | 0.2 + 0.3 | 3.6 | 4.1 | 4.8 |
| 15 | Partial condensation product made from 2,2'-dimethyl-4,4'-dihydroxy-5,5'-di-tert-butyldiphenyl sulfide with PCl₃ as in Example 2 | 0.5 | 3.1 | 3.2 | 4.2 |

The results of Table 2 show that the novel partial condensation product as in Example 2 shows excellent processing stabilization properties in Example 15 and even after five processing steps the original properties of the polymer are practically unchanged. Example 14 is the comparison with a known stabilizer combination.

Examples 16 to 20

Stabilizing action of the novel partially condensed stabilizer mixture in polypropylene without contact with copper.

100 parts of polypropylene powder are pelletized with 0.1 part of calcium stearate and with the amounts of stabilizers given in Table 1 in an extruder, with a short-compression-zone screw of length 450 mm and L/D ratio of 20, through 3 heating zones at 200° C., 230° C. and 230° C., and then sheets of 1 mm thickness were injection molded from the pellets through 4 heating zones at 210° C., 220° C., 230° C. and 240° C., with a screw diameter of 36 mm and L/D ratio of 25.

| Example No. | Stabilizer | Concentration [phr] | Embrittlement time at 140° C. [d] |
|---|---|---|---|
| 20 | Partial condenstaion product made from 2,2'-dimethyl-4,4'-dihydroxy-5,5'-di-tert-butyldiphenyl sulfide with PCl₃ (as in Example 2) + distearyl disulfide | 0.5 0.15 | 186 |

The stabilizing properties of the novel partially condensed stabilizer mixture as in Example 16 are apparent in comparison to the unstabilized polymer in Ex. 19.

In addition, synergistic stabilizer mixtures made from the novel partially condensed stabilizer mixture and phenolic antioxidants and, if desired, sulfur costabilizers, show considerably better action than the individual products themselves. Example 20 shows an example of this for a sulfur costabilizer. The resultant test specimens are stored in a temperature-controlled circulating air oven at the stated temperature until degradation becomes visible via discoloration or cracking, or the specimens break when subjected to 180° bending. High values to embrittlement in the accelerated aging in the circulating air oven demonstrate good stabilization.

TABLE 3

Long-term heat resistance of polypropylene in days:

| Example No. | Stabilizer | Concentration [phr] | Embrittlement time at 140° C. [d] |
|---|---|---|---|
| 16 | Partial condensation product made from 2,2'-dimethyl-4,4'-dihydroxy-5,5'-di-tert-butyldiphenyl sulfide with PCl₃ (as in Example 2) | 0.5 | 33 |
| 17 | Glycol bis[3,3-bis(4'-hydroxy-3'-tert-butylphenyl)butanoate] + distearyl disulfide | 0.2 + 0.3 | 204 |
| 18 | Glycol bis[3,3-bis(4'-hydroxy-3'-tert-butylphenyl)butanoate] + distearyl thiodipropionate + partial condensation product made from 2,2'-dimethyl-4,4'-dihydroxy-5,5'-di-tert-butyl-diphenyl sulfide with PCl₃ (as in Example 2) | 0.2 0.3 0.5 | 208 |
| 19 | none | 0.0 | 8 |

What is claimed is:

1. A stabilizer mixture obtainable by partial condensation of PCl$_3$ with 2,2'-dimethyl-4,4'-dihydroxy-5,5'-di-tert-butyidiphenyl sulfide wherein the stabilizer mixture has a phosphorous content of from 2 to 4% by weight and a content of 2,2'-dimethyl-4,4'-dihydroxy-5,5'-di-tert-butyldiphenyl sulfide of from 0.5 to 50% by weight.

2. The stabilizer mixture as claimed in claim 1, wherein the phosphorous content is from 2.3 to 3.5% by weight and the content of 2,2'-dimethyl-4,4'-dihydroxy-5,5'-di-tert-butyidiphenyl sulfide is from 8 to 35% by weight.

3. A process for preparing a stabilizer mixture having a phosphorous content of from 2 to 4% by weight and a content of 2,2'-dimethyl-4,4'-dihydroxy-5,5'-di-tert-butyldiphenyl sulfide of from 0.5 to 50% by weight comprising reacting PCl$_3$ (1) with 2,2'-dimethyl-4,4'-dihydroxy-5,5'-di-tert-butyldiphenyl sulfide (2) in a molar ratio (1):(2) of from 1:2.1 to 1:4.3.

4. The process as claimed in claim 3, wherein the reaction takes place in an organic solvent.

5. The process as claimed in claim 4, wherein the organic solvent is an aromatic organic solvent.

6. The process as claimed in claim 4, wherein the organic solvent is toluene or xylene.

7. The process as claimed in claim 3, wherein the reaction takes place at a temperature of from 20 to 150° C.

8. The process as claimed in claim 7, wherein the reaction takes place at a temperature of from 100 to 140° C.

9. The process as claimed in claim 8, wherein the reaction takes place at a temperature of from 115 to 130° C.

10. The process as claimed in claim 3, wherein the 2,2'-dimethyl-4,4'-dihydroxy-5,5'-di-tert-butyidiphenyl sulfide is initially charged in an organic solvent and the PCl$_3$ is added slowly over a period of from 0.5 to 8 hours.

11. The process as claimed in claim 10, wherein the PCl$_3$ is added slowly over a period of from 3 to 5 hours.

12. The process as claimed in claim 3, further comprising freeing a reaction product from volatile constituents over a period of from 2 to 10 hours at temperatures of up to 190° C. and at a pressure which may be reduced as far as 30 mbar.

13. A method of using a stabilizer mixture obtainable by partial condensation of PCl$_3$ with 2,2'-dimethyl-4,4'-dihydroxy-5,5'-di-tert-butyidiphenyl sulfide wherein the stabilizer mixture has a phosphorous content of from 2 to 4% by weight and a content of 2,2'-dimethyl-4,4'-dihydroxy-5,5'-di-tert-butyldiphenyl sulfide of from 0.5 to 50% by weight comprising adding the stabilizer mixture to an organic material to protect the organic material against damage caused by oxygen, light, and heat.

14. The method of using as claimed in claim 13, wherein the organic material is in contact with metals or metal ions.

15. The method of using as claimed in claim 13, wherein the organic material is selected from the group consisting of plastics, paints, coatings, and oils.

16. An organic material comprising a stabilizer mixture obtainable by partial condensation of PCl$_3$ with 2,2'-dimethyl-4,4'-dihydroxy-5,5'-di-tert-butyidiphenyl sulfide wherein the stabilizer mixture has a phosphorous content of from 2 to 4% by weight and a content of 2,2'-dimethyl-4,4'-dihydroxy-5,5'-di-tert-butyidiphenyl sulfide of from 0.5 to 50% by weight and wherein the stabilizer mixture is present in the organic material at a concentration of from 0.01 to 5% by weight.

17. The organic material as claimed in claim 16, wherein the concentration is from 0.05 to 2% by weight.

18. The organic material as claimed in claim 16, wherein the organic material is a polyolefin.

19. The organic material as claimed in claim 18, wherein the organic material is a crosslinked polyolefin.

20. The organic material as claimed in claim 18, wherein the organic material is polyethylene, polypropylene, or a copolymer of polyethylene or polypropylene.

21. The organic material as claimed in claim 16, wherein the organic material further comprises at least one additive selected from the group consisting of thio-costabilizers, phosphates, and phenolic antioxidants.

22. The organic material as claimed in claim 16, wherein the stabilizer mixture is present as a masterbatch.

* * * * *